US012097139B2

(12) United States Patent
Monden et al.

(10) Patent No.: US 12,097,139 B2
(45) Date of Patent: Sep. 24, 2024

(54) POSTURE AND LIFTING ORTHOTIC

(71) Applicants: Nancy Monden, Mililani, HI (US); Ashley Monden, Mililani, HI (US)

(72) Inventors: Nancy Monden, Mililani, HI (US); Ashley Monden, Mililani, HI (US)

( * ) Notice: Subject to any disclaimer, the term of this patent is extended or adjusted under 35 U.S.C. 154(b) by 275 days.

(21) Appl. No.: 16/784,896

(22) Filed: Feb. 7, 2020

(65) Prior Publication Data
US 2020/0170822 A1 Jun. 4, 2020

Related U.S. Application Data

(63) Continuation-in-part of application No. 13/953,008, filed on Jul. 29, 2013, now abandoned.

(60) Provisional application No. 61/700,669, filed on Sep. 13, 2012.

(51) Int. Cl.
*A61F 5/02* (2006.01)
*A61F 5/01* (2006.01)

(52) U.S. Cl.
CPC .............. *A61F 5/026* (2013.01); *A61F 5/028* (2013.01); *A61F 2005/0153* (2013.01)

(58) Field of Classification Search
CPC .............. A61F 5/02–03; A61F 5/05808; A61F 5/24–37; A61F 5/04–058; A61F 2005/0153; A41D 13/05; A41D 13/0506; A41D 13/0525; A41D 13/0518; A41D 13/0531; A45F 3/04–15; A45F 2003/045; A45F 2003/144
See application file for complete search history.

(56) References Cited

U.S. PATENT DOCUMENTS

| | | | |
|---|---|---|---|
| 245,655 A * | 8/1881 | Phelps | A61F 5/028 2/310 |
| 3,797,718 A | 3/1974 | Plant | |
| 4,154,381 A | 5/1979 | Zufich | |
| 4,593,697 A | 6/1986 | Salort | |
| 5,040,524 A * | 8/1991 | Votel | A61F 5/028 2/310 |
| 5,135,470 A | 8/1992 | Reeves | |
| 5,499,965 A * | 3/1996 | Sanchez | A61F 5/028 128/100.1 |
| 5,776,087 A * | 7/1998 | Nelson | A61F 5/026 602/19 |
| 5,806,740 A | 9/1998 | Carlson | |
| 5,988,315 A * | 11/1999 | Crane | A62B 35/0018 182/3 |
| 6,006,365 A | 12/1999 | Strandberg | |
| 6,280,405 B1 | 8/2001 | Broselid | |
| 6,450,131 B1 | 9/2002 | Broman | |
| 7,785,282 B2 | 8/2010 | Rauch | |
| 7,901,371 B1 | 3/2011 | Vayntraub | |

(Continued)

*Primary Examiner* — Michelle J Lee
(74) *Attorney, Agent, or Firm* — Boudwin Intellectual Property Law, LLC; Daniel Boudwin

(57) ABSTRACT

The present invention describes an orthotic back brace. The device comprises shoulder poster straps that are attached to a first waist belt. The shoulder posture straps tighten around the shoulders of the user when the user leans forward, thereby preventing the form of motion. Instead this system will force the user to bend at the knees keeping proper lifting posture. The device can be utilized to prevent back injuries, to support the back, and promote proper posture, which can cut down on back related injuries in the workplace.

4 Claims, 9 Drawing Sheets

(56) References Cited

U.S. PATENT DOCUMENTS

| | | |
|---|---|---|
| 8,172,117 B2 | 5/2012 | Maggi |
| 2001/0020144 A1 | 9/2001 | Heinz et al. |
| 2003/0212355 A1 | 11/2003 | Shilling |
| 2007/0027419 A1 | 2/2007 | Drennan |
| 2010/0318010 A1 | 12/2010 | Sandifer et al. |
| 2011/0077567 A1 | 3/2011 | Bledsoe |

\* cited by examiner

POSTURE AND LIFTING ORTHOTIC

CROSS REFERENCE TO RELATED APPLICATIONS

This application claims the benefit of U.S. application Ser. No. 13/953,008 filed on Jul. 29, 2013 which claims the benefit of U.S. Provisional Application No. 61/700,669 filed on Sep. 13, 2012, entitled "Posture Mechanics". The above identified patent application is herein incorporated by reference in its entirety to provide continuity of disclosure.

BACKGROUND OF THE INVENTION

The invention relates to an orthotic device. More specifically the invention pertains to a back brace that comprises a shoulder posture strap that is attached to a system of pulleys.

Active individuals do not often utilize proper posture and form techniques when handling and moving large or heavy items, which could be very dangerous, time consuming and difficult. Commonly performed incorrect lifting mechanics can cause back injuries in the workplace and at home, which can lead to costly injuries. Orthotic devices are externally applied on the user's body to alter the functional characteristics of the skeletal system. These devices are used to restrict body movement, reduce forces on a particular portion of the skeletal system, and aid in rehabilitation.

There are several back bracing systems of prior art which attempt to adjust incorrect posture mechanics. These devices are adapted to provide support to the back by immobilization of the torso. These braces act on the upper body by way of rigid chest plates, elastic or inelastic restrictive straps, and corset-like torso tightening devices. The use of such devices can be problematic in that they are often bulky, not uniquely adjustable and not suitable for use by an active person.

The present invention relates to a new and improved back brace assembly having a shoulder posture strap that is attached to a system of pulleys at the waist. Specifically the bracing system comprises a waist tightening belt, a pulley system attached thereto, and shoulder straps secured around the pulleys that are designed to prevent hunching when the user leans forward, thereby preventing the user from leaning forward and instead making the user bend at the knees. The device can be used to prevent back injuries, to support the back, and promote proper posture, which reduces back injuries in the workplace and promotes the learned behavior of proper posture and body mechanics.

Devices have been disclosed in the prior art that relate to back bracing devices. These include devices that have been patented and published in patent application publications. These devices generally relate to the total or the substantial immobilization of the torso area by the use of inelastic or immovable straps and bulky chest coverings that result in an uncomfortable fitting. The following is a list of devices deemed most relevant to the present disclosure, which are herein described for the purposes of highlighting and differentiating the unique aspects of the present invention, and further highlighting the drawbacks existing in the prior art.

Specifically, U.S. Pat. No. 5,135,470 to Reeves describes a shoulder and back support brace that is designed to help people who have preexisting back problems by placing the spine under compression. The brace comprises flexible elastic attachment straps that are adapted to fit over the shoulders and back. These straps are connected to the brace by hook and loop fasteners and perform the step of exerting a multitude of forces to the back and shoulder region in order to pull the shoulders back and prevent slumping. While the Reeves back support device is similar to the present invention, the present invention provides support to the back by using a pulley system that controls the forces acting on the user to provide a correcting posture and instead causes the user to perform a bending motion of the knees instead of using their back.

U.S. Pat. No. 6,450,131 to Broman describes a forward bending motion control harness that is designed to prevent lower back injuries caused by lifting and bending. The harness comprises flexible shoulder, back and foot straps that prevent the user from bending forward beyond a modifiable angle. Although the Broman harness is similar in nature to the present device and relevant to the present invention, the present invention provides an adjusting force on the back without the need of straps covering the majority of the length of the body.

U.S. Pat. No. 7,785,282 to Rauch describes a torso unit device for treating spinal orthosis. The device comprises a central torso unit with a sternal plate and several securing straps attached to the central unit that prevents a forward bending motion of the user via a spring based hinge. While the Rauch unit is similar in nature and relevant to the present invention in that it provides forces on the upper body, the present invention provides support of the torso by the use of a pulley system and without the use of a bulky central unit and a hinge that relay forces on the sternum of the user.

U.S. Published Patent Application Publication No. 2001/0020144 to Heinz et al. discloses a custom fitted orthotic device designed to be wrapped around the torso of the user by way of tightening pulleys that provide a corset-like compressed fitting around the torso of the user. The custom fitting orthotic device further comprises shoulder straps attached to a substantially rigid breast plate that prevents undesired movements by the user. While the Heinz orthotic device is similar in nature and relevant to the present invention in that it provides a restraining force on the upper body of the user, the present invention utilizes the pulley system about the shoulders to apply a corrective force onto the back.

Finally U.S. Published Patent Publication No. 2003/0212355 to Shilling describes a multi-purpose back brace that provides lumbar support by a waist belt and an attached pair of flexible straps. The Shilling device also describes how the straps are designed to be adjustable about the shoulders and knees of the user for use while either standing or sitting. Although the Shilling back brace is similar in nature and relevant to the present invention in that it offers support to the user while standing and sitting, however, the present invention accomplishes stabilization of the back by way of a pulley system located on either side of the body to apply a corrective force to user's back without the need of adjustment for situations in which the user is sitting or standing.

The present invention relates to a new and improved posture treatment device that provides a back brace assembly having a shoulder strap attached to a system of pulleys. Specifically, the pulley system acts by tightening about the shoulders user when the user leans forward, thereby preventing the s from incorrect leaning and thus hunching or slouching, and instead making the user bend at the knees when performing a lifting motion. The pulleys are located on either side of the user's waist and provide acting forces on the user's opposing shoulders to provide corrective forces against bending and flexion of the back in order to aid in promoting proper lifting behavior and body mechanics. In view of the drawbacks of the prior art devices, it is shown that the prior art has several known drawbacks and that the present invention is substantially divergent in design elements from the prior art and consequently it is clear that there is a need in the art for an improvement to existing posture correction devices. In this regard the instant invention substantially fulfills these needs.

SUMMARY OF THE INVENTION

In view of the foregoing disadvantages inherent in the known types of back bracing devices now present in the prior art, the present invention provides a new posture correction device wherein the same can be utilized for providing convenience for the user when back support and stabilization are necessary when lifting heavy or bulky objects.

It is therefore an object of the present invention to provide a new and improved posture correction device that has all of the advantages of the prior art and none of the disadvantages.

It is another object of the present invention to provide a posture correction device comprising a pulley system that is configured to provide a corrective force on the user's shoulders located on opposing sides of the pulley system.

Another object of the present invention is to provide a pulley system secured about a user's waistline.

Yet another object of the present invention is to provide a pulley-length adjusting mechanism to enable a customized suitable supporting force to a variety user body types.

Finally, an object of the present invention is to provide a device that prevents slouching or shrugging while lifting objects.

Other objects, features and advantages of the present invention will become apparent from the following detailed description taken in conjunction with the accompanying drawings.

BRIEF DESCRIPTION OF THE DRAWINGS

Although the characteristic features of this invention will be particularly pointed out in the claims, the invention itself and manner in which it may be made and used may be better understood after a review of the following description, taken in connection with the with the accompanying drawings wherein like numeral annotations are provided throughout.

DETAILED DESCRIPTION OF THE INVENTION

Figure 1:
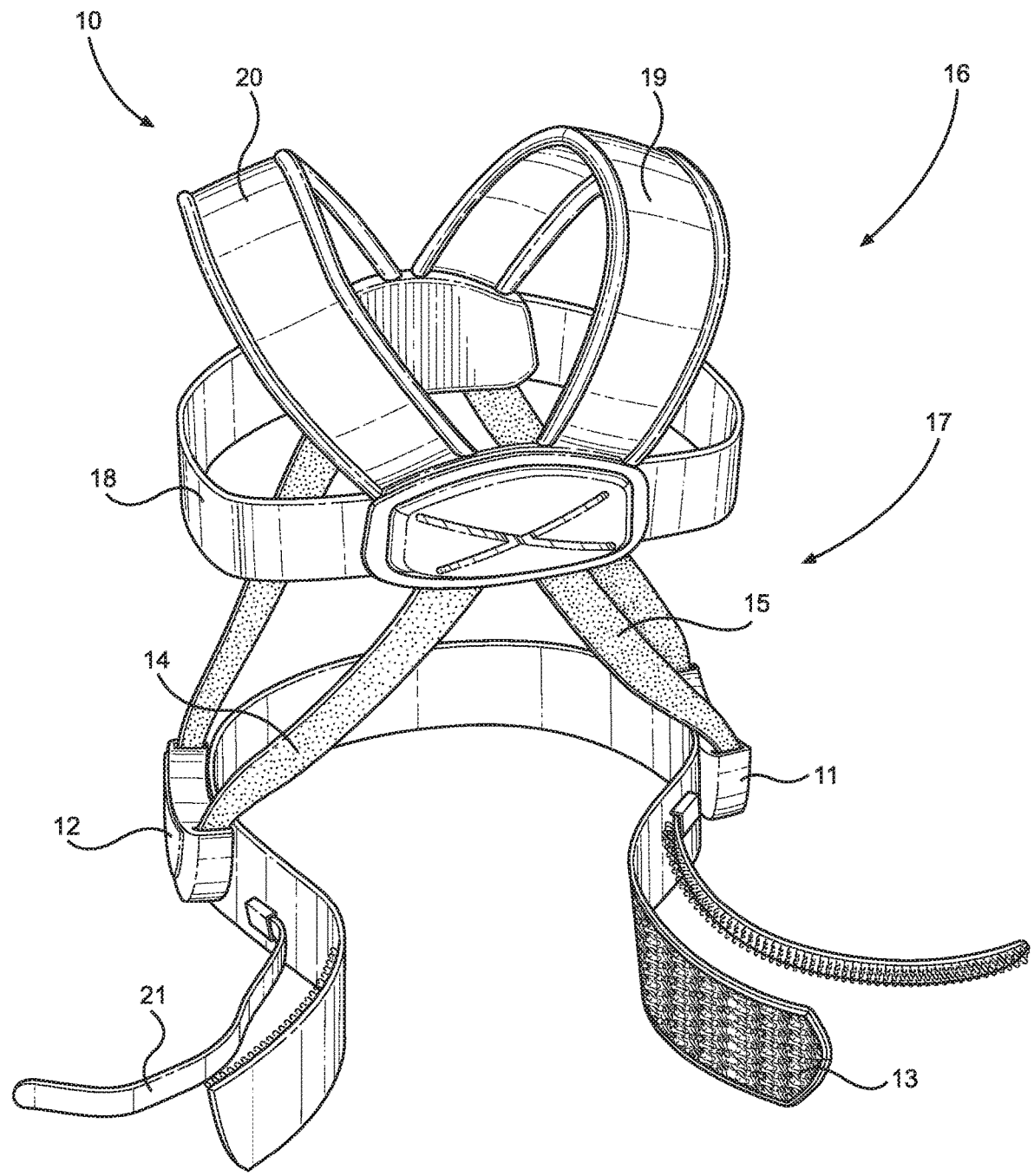
FIG. 1 shows a perspective view of the back brace.

Reference is made herein to the attached drawings. Like reference numerals are used throughout the drawings to depict like or similar elements of the orthotic back brace. For the purposes of presenting a brief and clear description of the present invention, the preferred embodiment will be discussed as used for posture correction and proper lifting techniques. The figures are intended for representative purposes only and should not be considered to be limiting in any respect.

Figure 2:
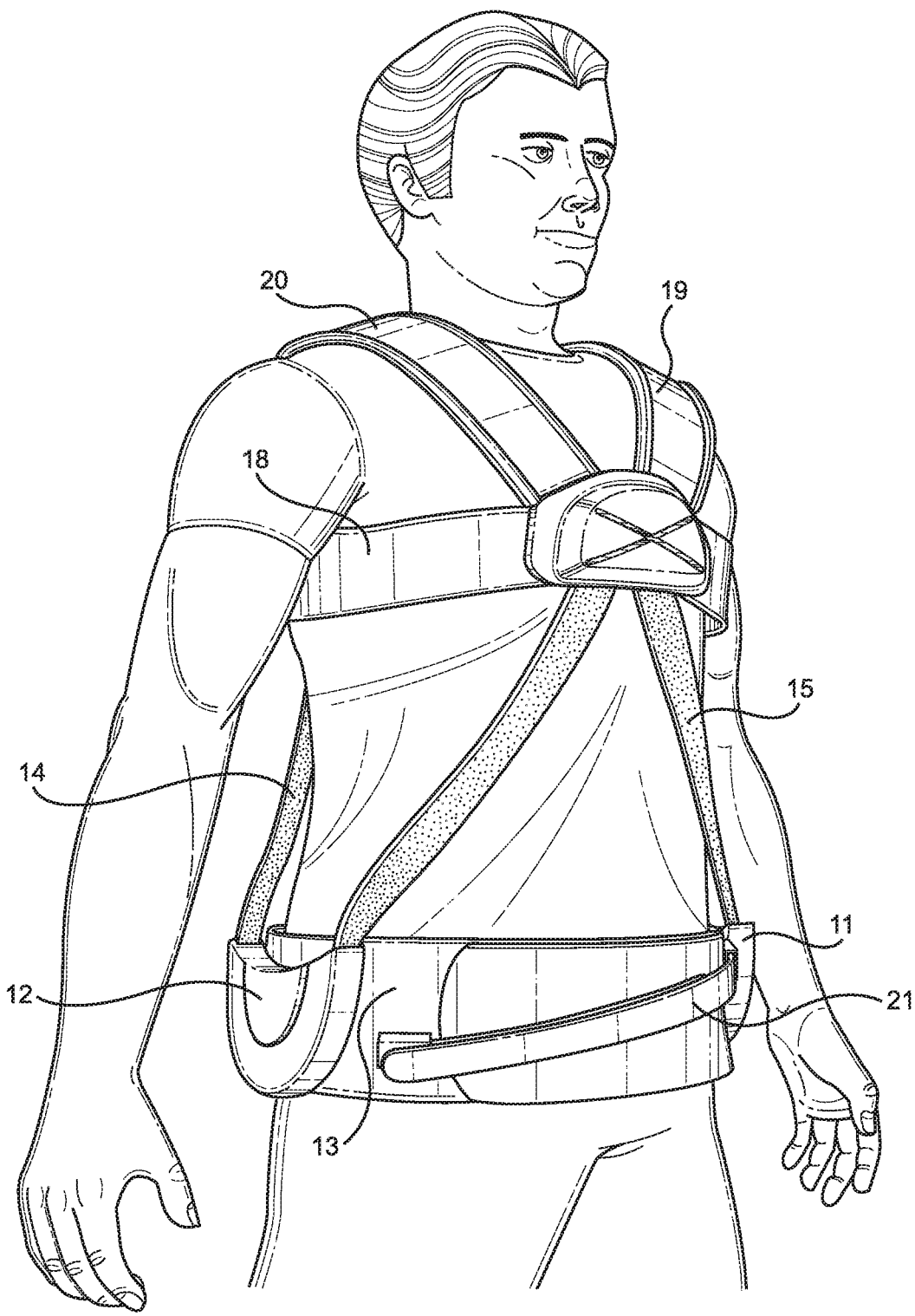
FIG. 2 shows a perspective view of the back brace while worn by the user.

Referring now to FIGS. 1 and 2, there are shown perspective views of the orthotic back bracing device 10. The back brace device 10 comprises an upper body assembly 16, a lower body assembly 17, and an adjustable lower waist belt 13. The upper body assembly 16 is comprised of a central chest strap 18 that is horizontally aligned and a pair of posture correcting shoulder straps 19 and 20. The lower body assembly is comprised of a set of pulley assemblies 11 and 12 secured to opposite sides of a lower waist belt 13. The pulley assemblies 11, 12 each contain an adjustable lower strap assembly 14, 15 that are connected to the upper body assembly at the central chest strap 18. The horizontal central chest strap 18 wraps around a wearer's chest and a wearer's upper back to secure the set of pulley assemblies 11, 12 each containing an adjustable lower strap assembly 17 to the wearer.

To allow for a customized fit, the orthotic back bracing device 10 provides a multitude of adjustable support straps. The device 10 is equipped with a customizable lower waist belt 13 comprising an adjustable hook and loop fastener strap 21 to provide a tightened fit around the waist of the user. The unit also comprises adjustable lower body straps 14, 15 that comprise the lower body assembly 17 and a central chest strap 18 and upper adjustable strap assemblies 19, 20 that comprise the upper body assembly. The upper 16 and lower 17 body assemblies are attached to each other at the central chest strap 18 of the upper body assembly 16.

Figure 3:
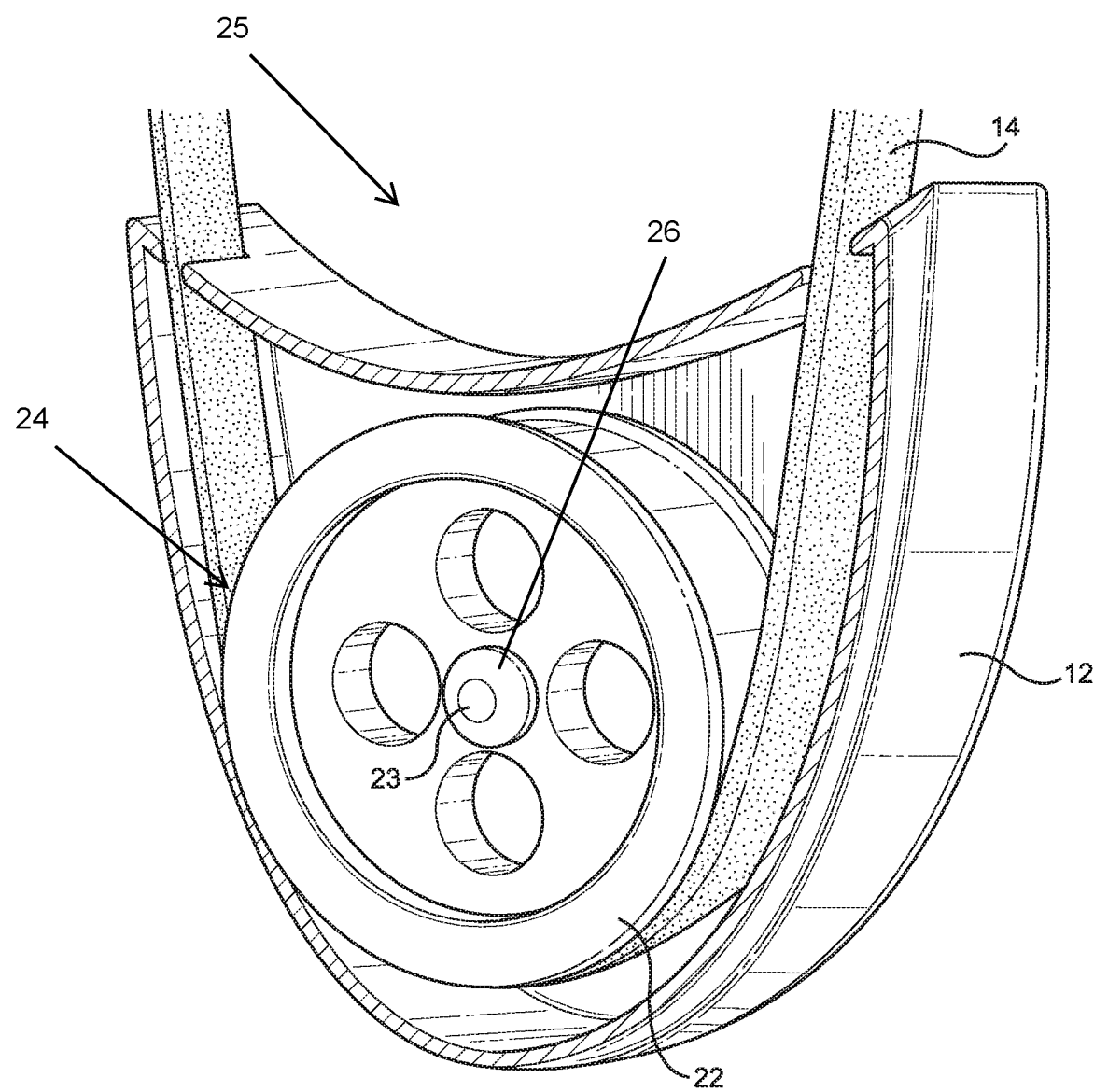
FIG. 3 shows a detailed view of the pulley mechanism of the present invention

Referring to FIG. 3, there is shown a detailed view of the components of the pulley assembly 11. The pulley assembly 11 is shown to be a free spinning pulley 24 within a housing 25 allowing a strap 14 to surround a low friction rotating pulley wheel 22 with a centrally located pin 23 from which the low friction rotating pulley wheel 22 rotates and promotes the movement of the lower strap system 14 with the associated movement of the wearer. The free spinning pulley 24 freely rotates about the centrally located pin 23 and may be supported using a pulley bearing 26 for free rotation thereof.

Figure 4:
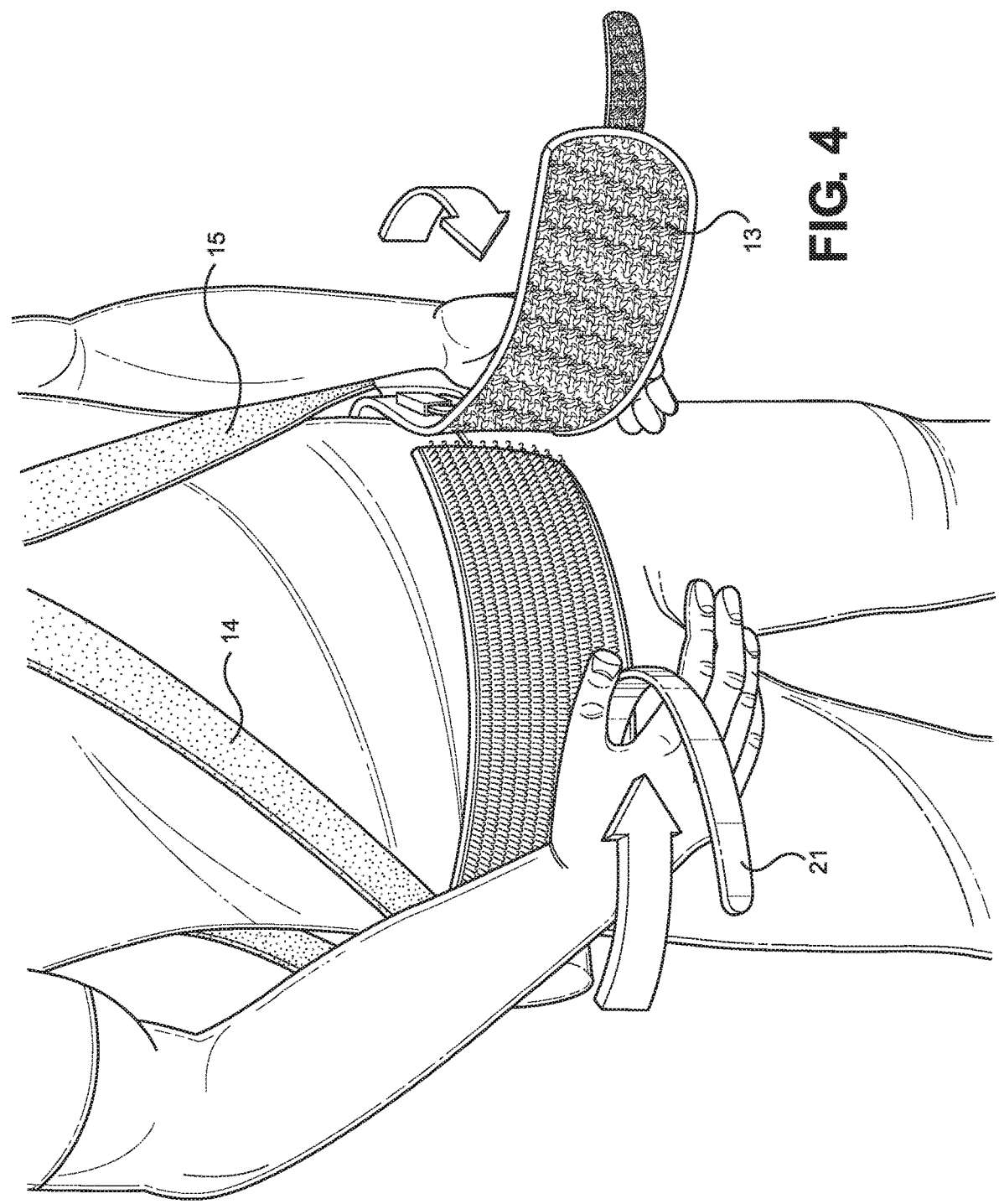
FIG. 4 shows a perspective view of the waist attachment mechanism of the present invention.

FIG. 4 shows a detailed view of the actions taken to correctly apply the orthotic back brace around the waist of the user. As shown, each side of the waist belt 13 comprises an attached fastener 21. The belt 13 is secured in place by locking one portion of the waist belt on to the opposite side of the belt. Examples of securement mechanisms 21 that are covered by the present invention are hook and loop fasteners (VELCRO), snap fittings, clasping mechanisms, strap tensioners, locking pulleys, etc. The securement mechanisms can be used to secure and adjust each of the components of the upper and lower body assemblies and allows the user to adjust the tightness of the belt around the body, thus enabling a therapeutic fitting.

Figure 5B:
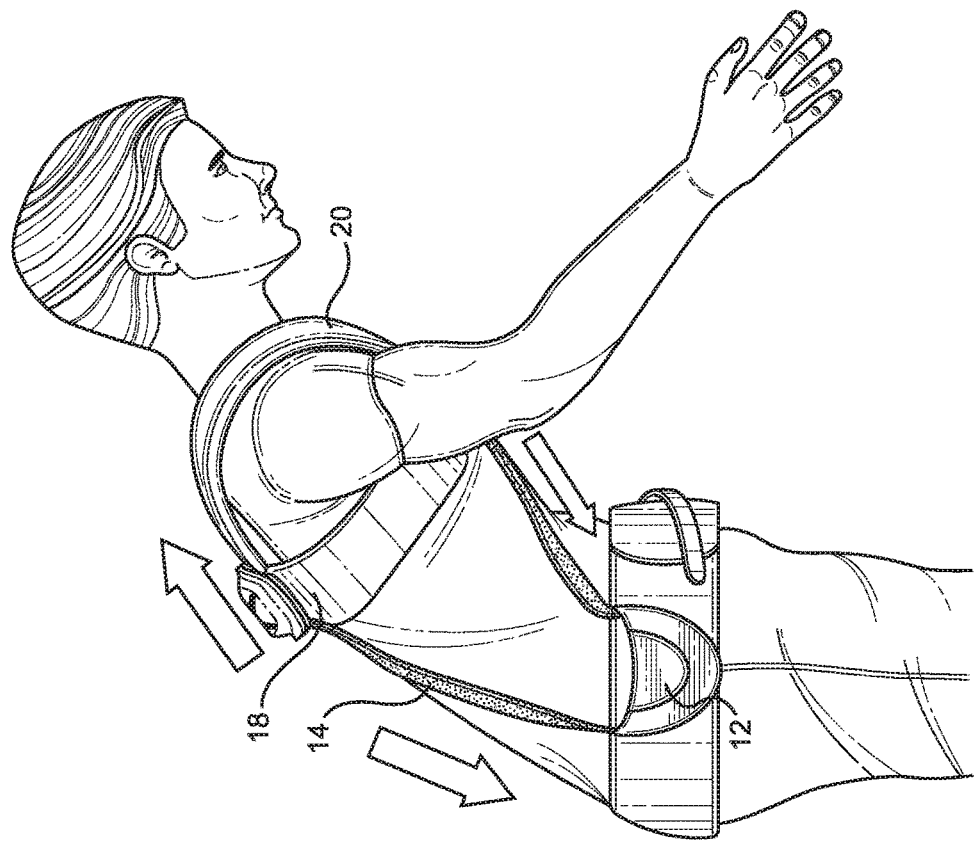
FIG. 5B shows a view of the forces applied onto the user by the present invention while performing a bending action.
Figure 5A:
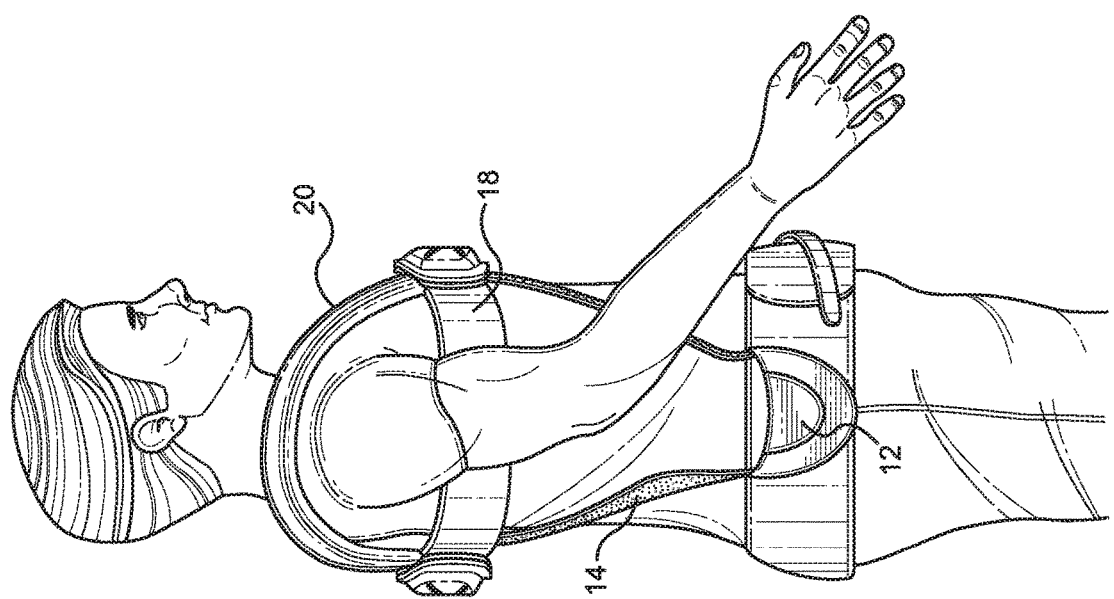
FIG. 5A shows a view of the forces applied onto the user by the present invention while standing.

FIGS. 5A and 5B detail the forces acted on the user by the back bracing device 10. As shown in FIG. 5A there are no forces acting on the user when a bending motion is not performed. A lack of substantial forces while in rest enables the bracing system to be used in times of leisure FIG. 5A, as well as during times of activity as in FIG. 5B. Alternate embodiments wherein the upper 19, 20 and lower straps 14, 15 are formed from one continuous piece and/or comprise additional paddings for added comfort are also covered within the scope of the present invention.

FIG. 5B details the actions of the bracing unit 10 on the user's upper body when performing a bending motion. When a bending motion is performed the forward movement of the adjustably fitted shoulder straps 19, 20 and accompanying lower straps 14, 15 cause the pulley wheel 22 of the pulley assembly 11 to rotate about the pin 23. The pulley assembly 11, 12, 14, 15 does not prevent a user from bending forward but instead enables one to maintain proper posture while performing a forward or sideways bend. The orthotic back brace device 10 utilizes the pulley assembly to tighten around the shoulders of a user when performing a bending action, thereby preventing hunching or shrugging of the shoulders while bending. This reactive bracing device prevents hunching, shrugging, and other injury promoting actions while lifting heavy or bulky objects, and instead promotes and teaches a proper posture stance which can cut down on back related injuries. The device is in contrast to a static orthotic that tends to restrict the user's motions rather than correct the posture of the user during the operation.

Figure 6:
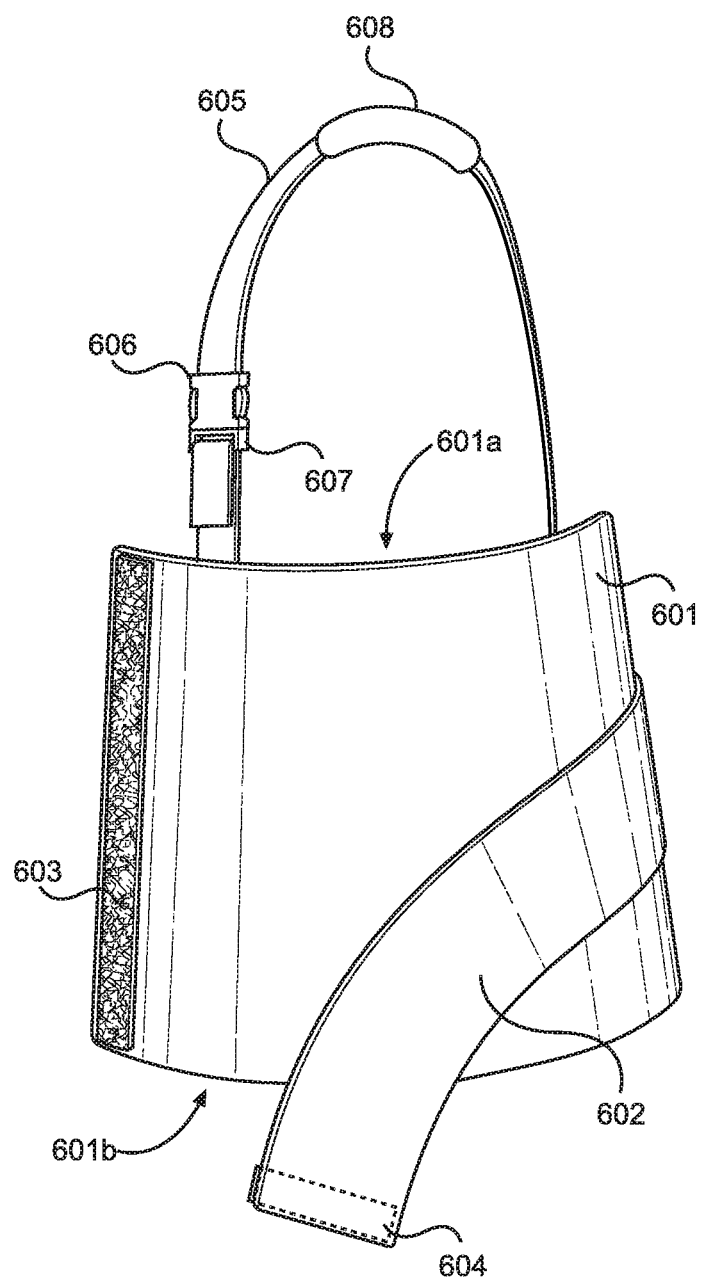
FIG. 6 shows a side view of an embodiment of the posture and lifting orthotic.

Referring now to FIG. 6, there is shown a side view of an embodiment of the posture and lifting orthotic. This embodiment of the posture and lifting orthotic is comprised of a first belt 601. The first belt 601 is configured to wrap around at least the waist of a human. In one embodiment, the first belt 601 is configured to fit a user such that a top side 601a of the first belt 601 is above the navel and a bottom side 601b of the first belt 601 is below the user's buttocks. In one embodiment, the first belt 601 is elastic. In one embodiment, the first belt 601 is adjustable. In a further embodiment, the first belt 601 is secured around a user using a securement device 603. In one embodiment, the securement device 603 is a hook and loop device. More specifically, the securement device 603 is vertically and linearly disposed along the width of the first belt 601.

In some embodiments, there is a waist belt 602. The waist belt 602 is configured to fit around the waist of a user. In this embodiment, the waist belt 602 is narrower than the first belt 601. The waist belt 602 is configured to add extra support to a user. In some embodiments, the waist belt 602 is secured to the first belt 601. In some embodiments, the waist belt 602 is elastic. The waist belt 602 secured around the user's waist using a securement device 604. In one embodiment, the securement device 604 is a hook and loop device. More specifically, the securement device 604 is coupled to the securement device 603.

In some embodiments there are shoulder straps 605 attached to the top side 601a of the first belt 601. In one embodiment the shoulder straps 605 have a detachable buckle 606. This buckle 606 will allow the straps 605 to be disconnected at one end. This will allow a user to easily put on and take off the device. In another embodiment the shoulder straps 605 have an adjustable length. In one embodiment the buckle 606 allows for the adjustment of the shoulder straps 605. In another embodiment there is an adjuster 607 that adjusts the shoulder straps 605. In some embodiments the shoulder straps 605 have shoulder pads 608. The shoulder pads 608 are located at a position that will allow the shoulder pads 608 to be on the top side of a wearer's shoulder.

Figure 7:
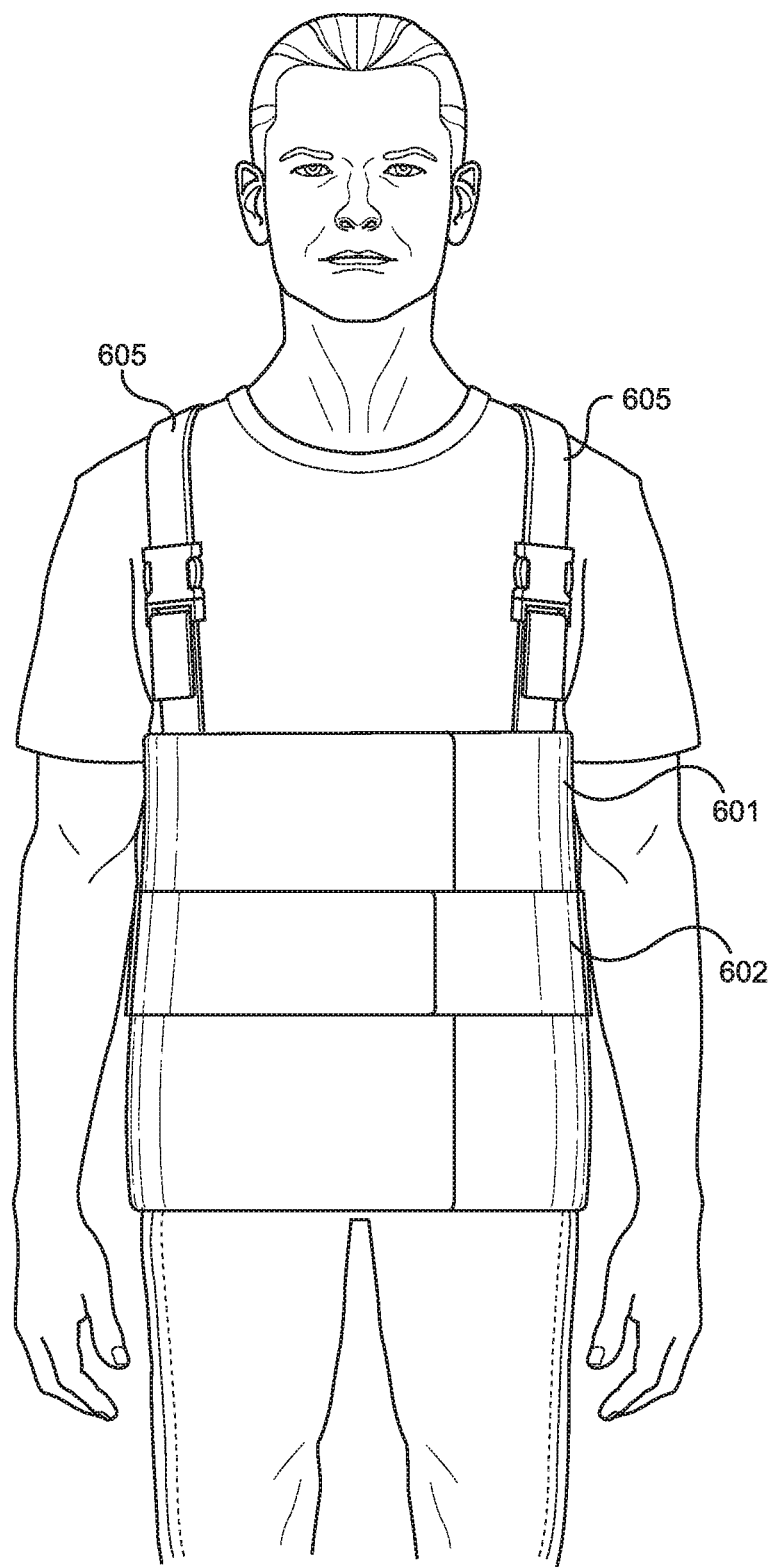
FIG. 7 shows a perspective view of an embodiment of the posture and lifting orthotic on a user.

Referring now to FIG. 7, there is shown a perspective view of an embodiment of the posture and lifting orthotic on a user. In use a wearer will attach the first belt 601 around their body. The first belt 601 will be located as described above. Next, a user will fix the shoulder straps 605 to the proper length. Lastly, the user secures the waist belt 602. The order in which the device is applied may vary. Once the device is secured the user will be restricted from bending at the waist. This will force an individual to have proper lifting posture. Further, the belts 601, 602 will give the user extra core support allowing them to lift more.

Figure 8:
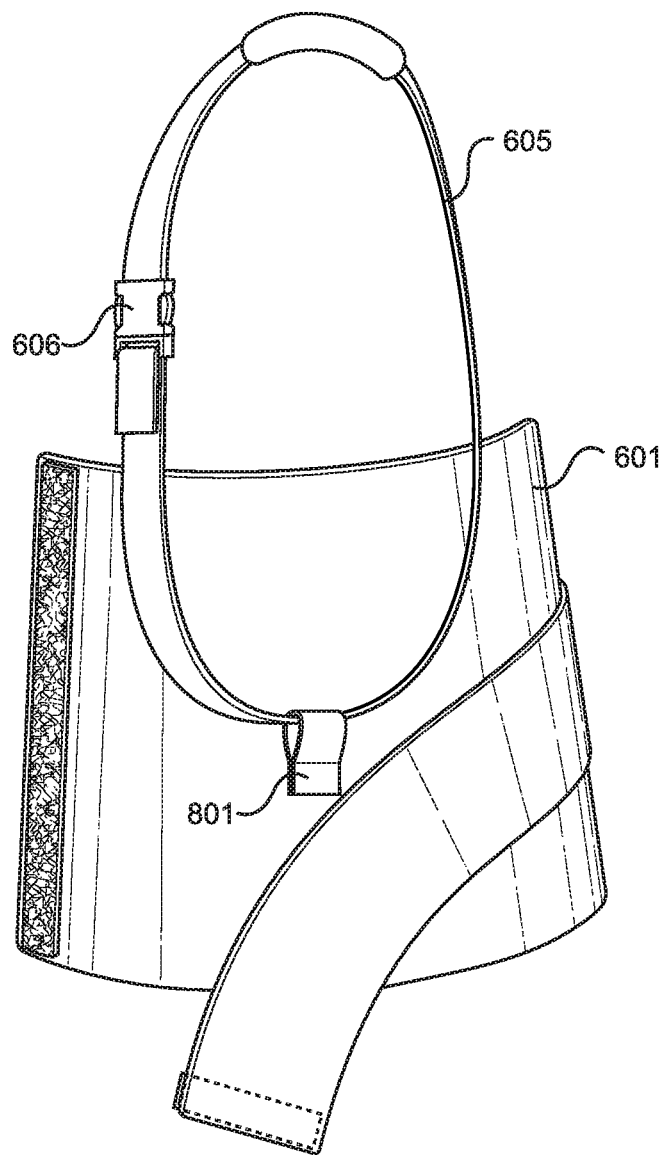
FIG. 8 shows a side view of an embodiment of the posture and lifting orthotic with movable straps.

Referring now to FIG. 8, there is shown a side view of an embodiment of the posture and lifting orthotic with movable straps. In some embodiments the shoulder straps 605 are dynamic shoulder straps. This means that the shoulder straps are configured to move as a user bends. This will allow the straps to maintain a constant pressure on the wearer instead of the straps loosening and tightening as the wearer bends. In one embodiment the dynamic functionality is accomplished via the connection the shoulder straps 605 have to the first belt 601. In this embodiment there is a connection loop 801 that is attached to the first belt 601 on each hip region. Each shoulder strap 605 is configured to be a continuous shoulder strap and to be located through the loop 801. In the embodiments where there are buckles 606, each shoulder strap 605 will be a continuous shoulder strap 605 when the buckles 606 are connected. This will allow the shoulder straps 605 to move as needed.

Figure 9:
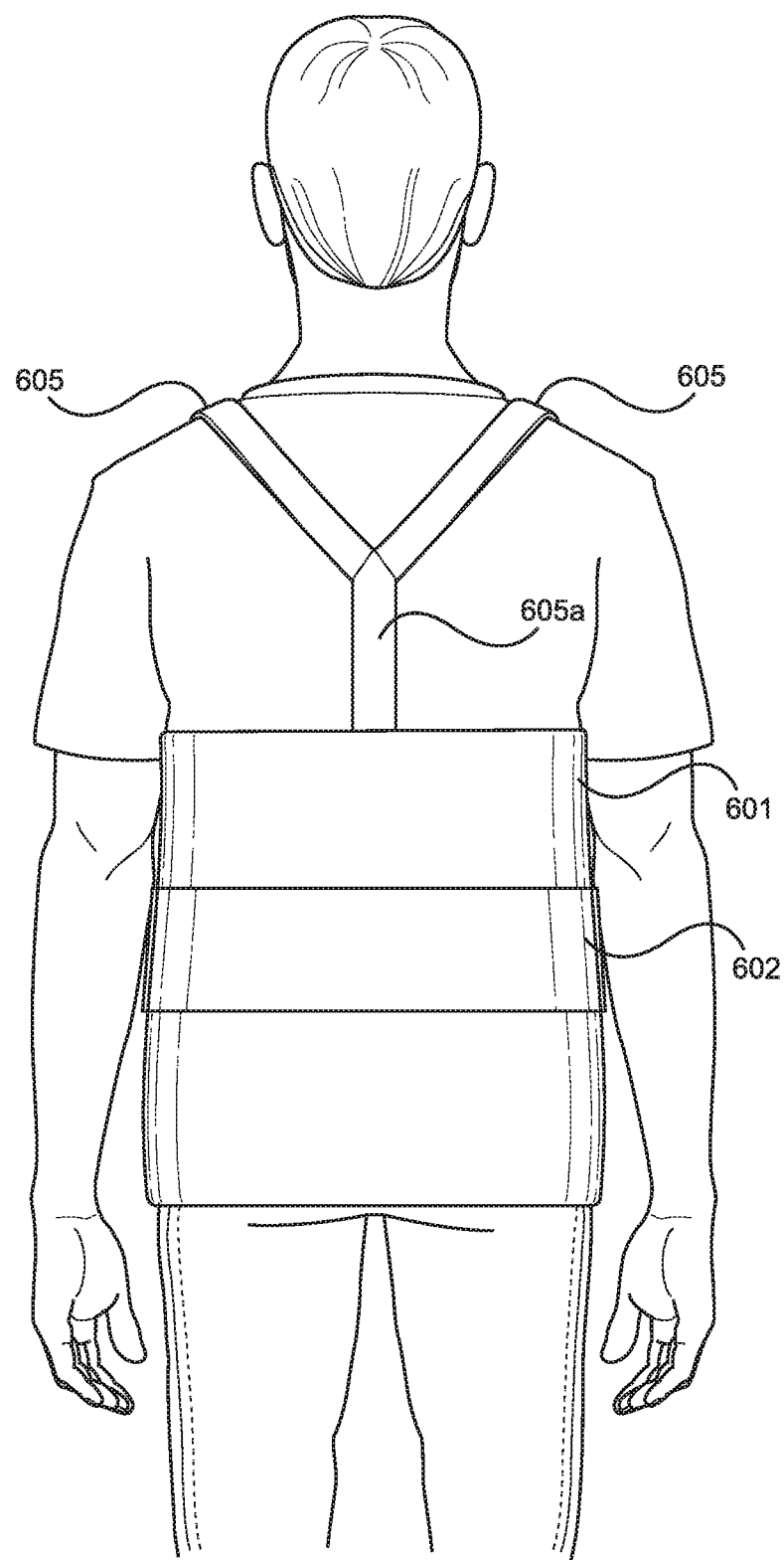
FIG. 9 shows a rear view of an embodiment of the posture and lifting orthotic.

Referring now to FIG. 9, there is shown a rear view of an embodiment of the posture and lifting orthotic. From this view an alternative embodiment of the shoulder straps 605 is shown. In this embodiment the shoulder straps 605 form a Y across a wearer's back. In the shown embodiment the shoulder straps 605 are attached to a shoulder strap connection strap 605a. The shoulder strap connection strap then connects to the belts 601, 602. The alternative embodiment will help to hold to shoulder straps in place when the device is used. The Y configuration will pull the shoulder straps 605 towards to middle of a user's back and prevent them from sliding from the shoulders.

It is therefore submitted that the instant invention has been shown and described in what is considered to be the most practical and preferred embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

We claim:
1. An orthotic back bracing device, comprising:
an adjustable lower waist belt configured to apply pressure to a wearer;
wherein the adjustable lower waist belt is adapted to fit around the wearer's waist;
a pair of shoulder straps extending between a central anterior portion and a central posterior portion of a horizontal central chest strap; and
a set of pulley assemblies each containing an adjustable lower strap assembly, each pulley assembly being on a respective lateral side of the waist belt and configured to be located along a frontal plane of the wearer when worn;

wherein each adjustable lower strap assembly extends from the central anterior portion, to its respective pulley assembly, and to the central posterior portion;

wherein the horizontal central chest strap is adapted to wrap around the wearer's chest and the wearer's upper back to secure the set of pulley assemblies to the wearer;

wherein the set of pulley assemblies are each a free spinning pulley within a housing allowing each adjustable lower strap assembly to surround a rotating pulley wheel with a centrally located pin from which the rotating pulley wheel is configured to rotate and promote movement of the respective adjustable lower strap assembly with an associated movement of the wearer, the free spinning pulley freely rotates about the centrally located pin and is supported using a pulley bearing for free rotation thereof.

2. The orthotic back bracing device of claim 1, wherein each of the pair of shoulder straps are adjustable.

3. The orthotic back bracing device of claim 1, wherein each of the pair of shoulder straps comprises padding.

4. The orthotic back bracing device of claim 1, wherein the adjustable lower waist belt is secured via a hook and loop fastener.

* * * * *